United States Patent
Fell et al.

(10) Patent No.: US 7,090,667 B2
(45) Date of Patent: Aug. 15, 2006

(54) ABSORBENT ARTICLE HAVING A MULTILAYER BLENDED CORE AND A METHOD OF FORMING

(75) Inventors: David Arthur Fell, Neenah, WI (US); William Anthony Georger, Neenah, WI (US); Jody Dorothy Suprise, Pine River, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 175 days.

(21) Appl. No.: 10/308,428

(22) Filed: Dec. 2, 2002

(65) Prior Publication Data

US 2003/0083630 A1 May 1, 2003

Related U.S. Application Data

(62) Division of application No. 09/854,360, filed on May 11, 2001.

(51) Int. Cl.
*A61F 13/20* (2006.01)

(52) U.S. Cl. .................................... 604/398
(58) Field of Classification Search ................. 604/365, 604/374, 379, 381, 378, 385.01, 385.23; 156/60

See application file for complete search history.

(56) References Cited

U.S. PATENT DOCUMENTS

| | | | |
|---|---|---|---|
| 4,592,943 A | 6/1986 | Cancian et al. | |
| 4,610,678 A | 9/1986 | Weisman et al. | |
| 4,670,011 A * | 6/1987 | Mesek | |
| 4,673,402 A | 6/1987 | Weisman et al. | |
| 5,037,409 A * | 8/1991 | Chen et al. | 604/358 |
| 5,188,624 A | 2/1993 | Young, Sr. et al. | |
| 5,334,177 A | 8/1994 | Cohen | |
| 5,342,336 A * | 8/1994 | Meirowitz et al. | 604/378 |
| 5,364,382 A | 11/1994 | Latimer et al. | |
| 5,429,629 A | 7/1995 | Latimer et al. | |
| 5,429,631 A | 7/1995 | Grenier | |
| 5,486,166 A | 1/1996 | Bishop et al. | |
| 5,486,167 A | 1/1996 | Dragoo et al. | |
| 5,490,846 A | 2/1996 | Ellis et al. | |
| 5,562,645 A | 10/1996 | Tanzer et al. | |
| 5,562,646 A | 10/1996 | Goldman et al. | |
| 5,651,862 A | 7/1997 | Anderson et al. | |
| 5,720,738 A | 2/1998 | Clark | |
| 5,728,082 A | 3/1998 | Gustafsson et al. | |
| 5,836,929 A | 11/1998 | Bewick-Sonntag et al. | |
| 5,891,119 A | 4/1999 | Ta et al. | |
| 5,916,507 A | 6/1999 | Dabi et al. | |
| 5,916,670 A | 6/1999 | Tan et al. | |
| 6,059,764 A * | 5/2000 | Osborn et al. | 604/385.22 |
| 6,068,620 A | 5/2000 | Chmielewski | |
| 6,096,015 A * | 8/2000 | Yeo et al. | 604/371 |
| 6,486,379 B1 * | 11/2002 | Chen et al. | 604/378 |
| 6,506,959 B1 * | 1/2003 | Hamajima et al. | 604/367 |
| 6,575,952 B1 * | 6/2003 | Kirk et al. | 604/386 |
| 6,734,335 B1 | 5/2004 | Graef et al. | |
| 2002/0169430 A1 * | 11/2002 | Kirk et al. | 604/378 |

FOREIGN PATENT DOCUMENTS

| | | |
|---|---|---|
| EP | 0 558 889 B1 | 3/1996 |
| EP | 0 719 531 A1 | 7/1996 |
| EP | 1 057 465 A1 | 12/2000 |
| FR | 2 656 794 A1 | 7/1991 |
| WO | WO 98/47456 A1 | 10/1998 |
| WO | WO 99/63922 A1 | 12/1999 |
| WO | WO 99/63923 A1 | 12/1999 |
| WO | WO 99/63925 A1 | 12/1999 |
| WO | WO 00/29658 A1 | 5/2000 |
| WO | WO 00/59439 A1 | 10/2000 |

* cited by examiner

*Primary Examiner*—James Housel
*Assistant Examiner*—Angela J Grayson
(74) *Attorney, Agent, or Firm*—Thomas J. Connelly (57) ABSTRACT

An absorbent article, such as a thin incontinence pad or pantyliner, is disclosed which has an absorbent core formed from multiple layers of blended material for providing protection against involuntary urine loss. A method of forming the absorbent article is also disclosed. The absorbent article includes a liquid permeable bodyside liner, a liquid-impermeable baffle, and first and second absorbents positioned between the liner and the baffle. The first absorbent is a stabilized material containing a superabsorbent and has a predetermined basis weight. The second absorbent is also a stabilized material containing a superabsorbent. The second absorbent is positioned below the first absorbent and has a basis weight that is at least equal to the basis weight of the first absorbent.

14 Claims, 2 Drawing Sheets

ABSORBENT ARTICLE HAVING A MULTILAYER BLENDED CORE AND A METHOD OF FORMING

This is a divisional of application Ser. No. 09/854,360, filed May 11, 2001.

FIELD OF THE INVENTION

This invention relates to an absorbent article having a multilayer blended core for containing bodily exudate, especially urine and a method of forming the article. More specifically, this invention relates to a thin incontinence pad or pantyliner for absorbing and retaining body fluids.

BACKGROUND OF THE INVENTION

Absorbent articles such as catamenial pads, sanitary napkins, pantyliners, and the like, are designed to be worn adjacent to a woman's pudendum to absorb body fluid such as menses, blood, urine and other body excretions. It has been found that many women suffering from incontinence will buy and use a feminine care product, such as a pantyliner or a sanitary napkin, for the purpose of absorbing and retaining urine. Many incontinent men will also buy and/or wear feminine care products since they are readily, commercially available and these products may also be present in their household.

Incontinence users experience important differences from menstruating women and the use of commercially available feminine care products may not satisfy their specific needs. Most incontinence users require a product that can absorb and retain urine over an extended period of time. Since feminine care products are specifically designed to absorb and retain menses, many do not contain superabsorbents. Superabsorbents are capable of retaining large quantities of body fluid, such as urine, but it is known that they can impede the flow of menses. Without the presence of superabsorbents, many feminine care products do not have the fluid retention capacity needed by incontinence users. The presence of superabsorbents in incontinence products allows the liquid urine to be locked away so the product feels dry to the wearer. Many incontinence users tend to expel only a few drops of urine at a time and therefore they tend to wear their products over a longer time period. In addition, many incontinence users are older, frugal or on a fixed income and therefore some tend to wear their products for an extended period of time in order to save money. Another reason many incontinence users wear pantyliners or ultra thin catamenial pads for incontinence is that most incontinence products are thick and bulky rather than being thin and discreet. In our society, incontinence users have a strong psychological reason for not wanting other people to know that they suffer from incontinence.

Because of the above concerns, there is a need to produce a relatively inexpensive, thin incontinence pad or pantyliner, having a thickness of less than about 5 millimeters, which can absorb and retain from between about 20 grams (g) to about 100 grams of urine.

Now, a relatively inexpensive, thin absorbent article has been invented that can do just that. This absorbent article contains an absorbent core formed from two or more layers of stabilized material, each containing a superabsorbent.

SUMMARY OF THE INVENTION

Briefly, this invention relates to an absorbent article, such as an incontinence pad or pantyliner, having an absorbent core formed from two or more layers of blended material for providing protection against involuntary loss of body fluids. A method of forming the absorbent article is also taught. The absorbent article includes a liquid permeable bodyside liner, a liquid-impermeable baffle, and first and second absorbents positioned between the liner and the baffle. The first absorbent is a stabilized material containing a superabsorbent and has a predetermined basis weight. The second absorbent is also a stabilized material containing a superabsorbent. The second absorbent is positioned beneath the first absorbent and has a basis weight that is at least equal to, and preferably, greater than the basis weight of the first absorbent.

The general object of this invention is to provide an absorbent article that has an absorbent core constructed from two or more layers of stabilized material for containing body fluid involuntarily expelled from a human body. A more specific object of this invention is to provide a thin incontinence pad or pantyliner for absorbing and retaining urine and a method of forming the product.

Another object of this invention is to provide an absorbent article that has a thickness of less than about 5 millimeters.

A further object of this invention is to provide a thin absorbent article that utilizes an absorbent core formed from two or more layers of airlaid material, each containing a superabsorbent.

Still another object of this invention is to provide a thin absorbent article that has an absorbent core constructed from two or more layers of airlaid, each layer containing a superabsorbent, and the second absorbent has a basis weight at least equal to the basis weight of the first absorbent.

Still further, an object of this invention is to provide a reasonably priced, thin absorbent article that is easy to manufacture.

Other objects and advantages of the present invention will become more apparent to those skilled in the art in view of the following description and the accompanying drawings.

DETAILED DESCRIPTION OF THE PREFERRED EMBODIMENTS

Figure 1:
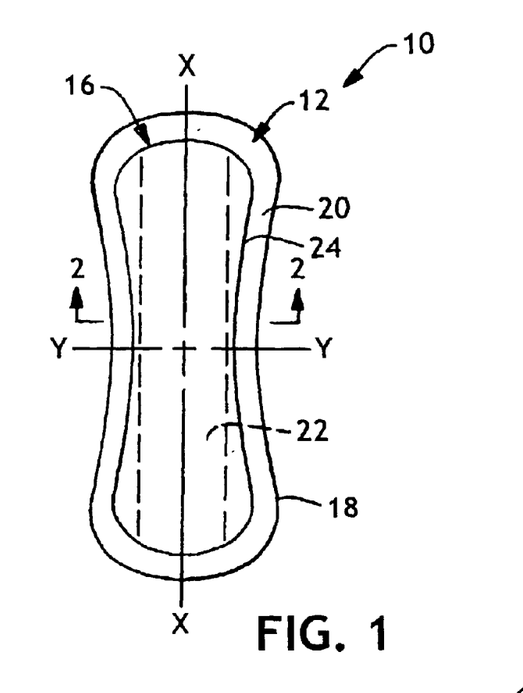
FIG. 1 is a top view of an absorbent article such as a thin incontinence pad or a pantyliner designed to absorb and retain urine.
Figure 2:
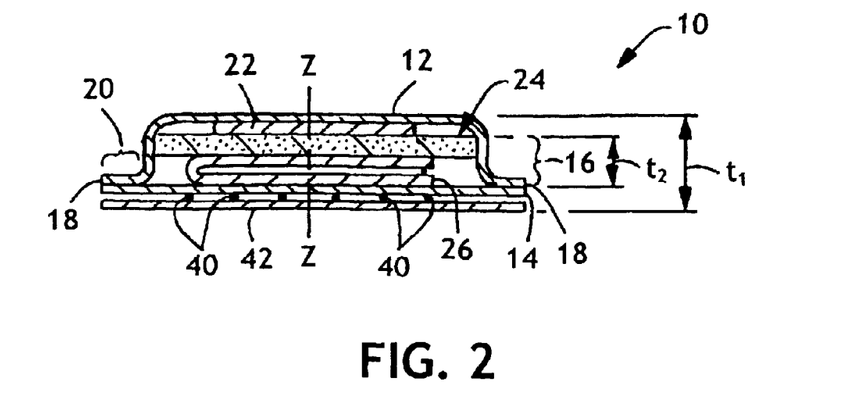
FIG. 2 is a cross-sectional view of the absorbent article shown in FIG. 1 taken along line 2—2 and showing the first and second absorbents forming the absorbent core.

Referring to FIGS. 1 and 2, an absorbent article 10 is shown which is depicted as a thin incontinence pad or pantyliner. The absorbent article 10 is designed to be secured to an inside surface of a person's undergarment by a garment adhesive and is designed to absorb and retain urine that is involuntarily expelled from the body. The absorbent article 10 is an elongated product having a central longitudinal axis x—x, a central transverse axis y—y, and a vertical axis z—z. The absorbent article 10 is relatively thin. By "thin" it is meant that the absorbent article 10 has a thickness of less than about 5 millimeters. Preferably, the absorbent article 10 has a thickness of less than about 4 millimeters, and most preferably, the absorbent article 10 has a thickness of less than about 3.5 millimeters. The absorbent article 10 has a fluid retention capacity capable of absorbing from between about 20 grams to about 100 grams of urine. Preferably, the absorbent article 10 will be able to absorb about 50 grams of urine.

The absorbent article 10 includes a liquid permeable liner or cover 12, a liquid-impermeable baffle 14, and an absorbent core 16 positioned and enclosed between the liner 12 and the baffle 14. The bodyside liner 12 is designed to be in contact with the wearer's body. The bodyside liner 12 can be constructed of a woven or nonwoven material that is easily penetrated by body fluid, especially urine. The liner 12 can also be formed from either natural or synthetic fibers. Suitable materials include bonded-carded webs of polyester, polypropylene, polyethylene, nylon or other heat-bondable fibers. Other polyolefins, such as copolymers of polypropylene and polyethylene, linear low-density polyethylene, finely perforated film webs and net materials, also work well. A suitable material is a soft, wettable homopolymer spunbond having a basis weight of from between about 13 grams per square meter (gsm) to about 27 gsm. Another suitable material is an apertured thermoplastic film. Still another preferred material for the bodyside liner 12 is a spunbond web of polypropylene. The spunbond web can contain from between about one percent (1%) to about six percent (6%) of titanium dioxide pigment to give it a clean, white appearance. When the liner 12 is constructed from a spunbond web, it is desirable to use a uniform thickness of spunbond because it will provide sufficient strength to resist being torn or pulled apart during use. The most preferred polypropylene webs have a basis weight of from between about 13 to about 40 grams per square meter (gsm). An optimum basis weight is from between about 15 gsm to about 25 gsm. The thickness of the bodyside liner 12 can range from between 0.1 millimeters mm to about 1.0 mm.

It should be noted the bodyside liner 12 could be coated, sprayed or otherwise treated with a surfactant to make it hydrophilic. By "hydrophilic" it is meant that the bodyside liner 12 will have a strong affinity for water. When the bodyside liner 12 is formed from a hydrophilic material, it will allow the body fluid to pass quickly therethrough. The bodyside liner 12 can also be embossed to improve the aesthetic appearance of the absorbent article 10.

The liquid permeable liner 12 and the liquid-impermeable baffle 14 cooperate to enclose and retain the absorbent core 16 therebetween. The liner 12 and the baffle 14 can be cut, sized and shaped to have a coterminous outer edge 18. When this is done the liner 12 and the baffle 14 can be bonded in face to face contact to form an absorbent article 10 having a peripheral seal or fringe 20. The peripheral fringe can be formed to have a width of about 5 millimeters. Preferably, the liner 12 and the baffle 14 will each have a generally dogbone or hourglass configuration. With a dog bone or hourglass configuration, the absorbent article 10 will have a narrow section located adjacent to the central transverse axis y—y that separates a pair of larger, end lobes. The end lobes can be sized and/or shaped differently, if desired. An absorbent article 10 having a dogbone or hourglass shape is more comfortable to wear than a generally rectangular shaped product. The absorbent article 10 can also be asymmetrical. The liner 12 and the baffle 14 can also be bonded or sealed together about their periphery by a construction adhesive to form a unitary absorbent article 10. Alternatively, the liner 12 and the baffle 14 can be bonded together by heat, pressure, by a combination of heat and pressure, by ultrasonics, etc. to form a secure attachment.

The liquid-impermeable baffle 14 can be designed to permit the passage of air or vapor out of the absorbent article 10 while blocking the passage of body fluid, such as urine. The baffle 14 can be made from any material exhibiting these properties. The baffle 14 can also be constructed from a material that will block the passage of vapor as well as fluids, if desired. A good material for the baffle 14 is a micro-embossed, polymeric film, such as polyethylene or polypropylene. Bicomponent films can also be used. A preferred material is polyethylene film. Most preferably, the baffle 14 will be comprised of a polyethylene film having a thickness in the range of from between about 0.1 mm to about 1.0 mm.

Referring again to FIG. 2, the absorbent article 10 is shown having a transfer layer 22. The transfer layer 22 is optional and can be eliminated if desired. The transfer layer 22, which may contain a plurality of apertures formed therethrough, is positioned between the bodyside liner 12 and the absorbent core 16 and is aligned along the central longitudinal axis x—x. Preferably, the transfer layer 22 is positioned immediately below the bodyside liner 12 and is in direct face to face contact therewith. The transfer layer 22 can be adhesively bonded to the absorbent core 16, if desired, in order to facilitate a transfer of body fluid therebetween. The transfer layer 22 can extend over a portion of the length of the absorbent core 16 or it can extend over the entire length of the absorbent core 16. Preferably, the transfer layer 22, when present, will extend over at least 70% of the length of the absorbent core 16. Although the transfer layer 22 is optional, when present, it does provide good fluid movement of the urine downward from the bodyside liner 12 into the absorbent core 16. This downward movement of the urine is parallel to the vertical axis z—z. The z-axis is perpendicularly arranged relative to the x and y-axes. In addition, the transfer layer 22 inhibits the flow of urine from the absorbent core 16 back up into the liner 12. This phenomenon is commonly referred to as rewet. It is important that incontinence pads and pantyliners do not exhibit rewet because the consumer views it as an undesirable feature.

The transfer layer 22 can be constructed from a material that will provide good fluid transfer. Typical materials that can be used for the transfer layer 22 are spunbond, coform and carded webs. One useful material is a wettable nonwoven having a basis weight of from between about 13 gsm to about 50 gsm. The transfer layer 22 can be treated to make it hydrophilic. The thickness of the transfer layer 22 can range from between about 0.2 mm to about 1.0 mm. The transfer layer 22 can also be dyed to a different color than the color of the bodyside liner 12 and/or the absorbent core 16. A light blue, pink, or peach color has been found to be desirable, as these are pleasing colors to the ultimate consumer. The transfer layer 22 can alternatively be white in color yet will still be distinguishable from the bodyside liner 12 which may have a different shade of white. A benefit of making the transfer layer 22 a different color than the absorbent core 16 is that it presents a fluid target for the wearer.

It should be noted that the transfer layer 22 could be embossed to improve the aesthetic appearance of the absorbent article 10 since the transfer layer 22 is visible beneath the bodyside liner 12.

It is also possible to substitute a surge layer (not shown) for the transfer layer 22. The purpose of a surge layer is to quickly take up and temporarily hold the urine until the absorbent core 16 has adequate time to absorb the urine. The surge layer can be formed from various materials. Two good materials from which the surge layer can be formed include a crimped bicomponent spunbond or from a bonded carded web. When a surge layer is utilized, it should be designed to have a basis weight of from between about 30 gsm to about 85 gsm and a thickness ranging from between about 0.15 mm to about 2 mm. The following U.S. Pat. Nos. teach search layers: U.S. Pat. Nos. 5,364,382; 5,429,629; 5,490,846 and 5,486,166.

Still referring to FIG. 2, the absorbent article 10 has an absorbent core 16 that is positioned between the transfer layer 22 and the liquid-impermeable baffle 14. If no transfer layer is present, the absorbent core 16 is positioned between the bodyside liner 12 and the liquid-impermeable baffle 14. The absorbent core 16 includes a first absorbent 24 and a second absorbent 26. The first absorbent 24 is arranged close to the liner 12 and is positioned vertically above the second absorbent 26. The first absorbent 24 should be in direct face to face contact with the second absorbent 26. The first absorbent 24 can be adhered, for example, by an adhesive, to the second absorbent to ensure intimate contact and better fluid transfer therebetween. The first absorbent 24 is an airlaid material. Airlaid materials are commercially available from several manufacturers. Concert GmbH is one such supplier of airlaid material that can be used to construct the absorbent article 10. Concert GmbH has an office located at Am Lehmberg 10, 16928 Falkenhagen, Germany.

Even though it is preferred that the first and second absorbents, 24 and 26 respectively, be in direct contact with one another, it is possible to place one or more layers of tissue therebetween. Some manufacturers like to wrap an absorbent containing superabsorbent particles so as to prevent the superabsorbent particles from escaping from the finished product.

Figure 3:
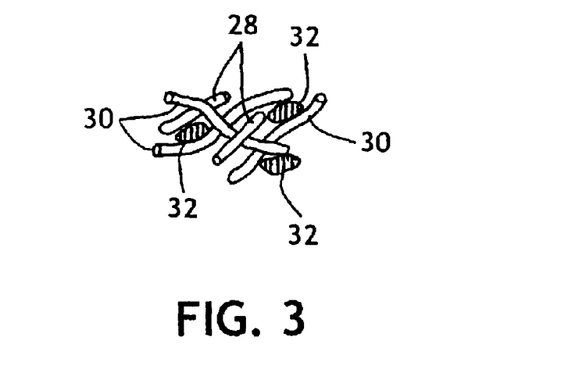
FIG. 3 is an enlarged view of a portion of the first absorbent shown in FIG. 2.

Referring now to FIG. 3, the first absorbent 24 is a stabilized material, preferably an airlaid material, constructed of a blend of a first group of fibers 28, a binder 30, preferably in the form of a second group of fibers, and a superabsorbent 32 which is cured to form a stabilized, airlaid absorbent structure. The first absorbent 24 also has a predetermined basis weight of from between about 100 gsm to about 600 gsm. Preferably, the first absorbent 24 has a basis weight of from between about 100 gsm to about 400 gsm. Most preferably, the first absorbent 24 has a basis weight of about 200 gsm. The first group of fibers 28 can be cellulosic fibers, such as pulp fibers, that are short in length, have a high denier, and are hydrophilic. The first group of fibers 28 can be formed from 100% softwood fibers. Preferably, the first group of fibers 28 are southern pine Kraft pulp fibers having a length of about 2.5 mm and a denier of greater than 2.0. The denier of cellulosic fibers can be determined by running a coarseness test on a Kajanni analyzer to obtain a coarseness value in the units of milligrams per 100 meters (mg/100 m). This coarseness value is then divided by a constant value 11.1 to obtain a common textile denier in the units of grams per 9000 meters (g/9000 m). A suitable material to use for the first group of fibers 28 is Weyerhaeuser NB 416 pulp fibers which is commercially available from Weyerhaeuser Company. Weyerhaeuser Company has an office located at 33650 6$^{th}$ Avenue South, Federal Way, Wash. 98003.

Referring again to FIG. 1, the first absorbent 24 is depicted as having a shaped periphery in the form of a dog bone configuration. Other shapes, such as an hourglass shape, an oval shape, a trapezoid shape, or an asymmetrical shape formed about the longitudinal axis, etc. can also be used. A peripheral shape, wherein the first absorbent 24 is narrowest in the middle along the central transverse axis y—y, works well for it will be more comfortable to wear. A trapezoidal or tapered configuration works well for a male incontinent product.

The binder portion of the first absorbent 24 can be a chemical coating. Preferably, the binder portion of the first absorbent 24 will consist of a second group of fibers 30. The second group of fibers 30 can be synthetic binder fibers. Synthetic binder fibers are commercially available from several suppliers. One such supplier is Trevira GmbH & Company KG having a mailing address of Max-Fischer-Strasse 11, 86397 Bobingen, Deutschland. Another supplier of binder fibers is Fibervisions a/s having a mailing address of Engdraget 22, Dk-6800 Varde, Denmark. A third supplier of binder fibers is KoSa having a mailing address of P.O. Box 4, Highway 70 West, Salisbury, N.C. 28145. Preferably, the second group of fibers 30 are bicomponent fibers having a polyester core surrounded by a polyethylene sheath. Alternatively, the second group of fibers 30 can be bicomponent fibers having a polypropylene core surrounded by a polyethylene sheath.

The fibers making up the second group of fibers 30 are longer in length and have a lower denier than the fibers making up the first group of fibers 28. The length of the fibers 30 can range from between about 3 mm to about 6 mm. A fiber length of 3 mm works well. The fibers 30 can have a denier of less than or equal to 2.0. The fibers, 30 should be moisture insensitive and can be either crimped or non-crimped. Crimped fibers are preferred since they process better.

The first absorbent 24 also contains a superabsorbent 32. A superabsorbent is a material that is capable of absorbing at least 10 grams of water per gram of superabsorbent material. The superabsorbent 32 is preferably in the shape of small particles, although fibers, flakes or other forms of superabsorbents can also be used. A suitable superabsorbent 32 is FAVOR 880. FAVOR 880 is commercially available from Stockhausen, Inc. having an office located at 2408 Doyle Street Greensboro, N.C. 27406. Other similar types of superabsorbents, some of which are commercially available from Stockhausen Inc., can also be used. Preferably, the superabsorbent 32 is present in a weight percent of from between about 10% to about 60%. It is important that the first absorbent 24 contain a superabsorbent to keep the user dry since it is closest to the user's body.

The individual components 28, 30 and 32 of the first absorbent 24 can be present in varying amounts. However, it has been found that the following percentages work well in forming the thin absorbent article 10. The first group of fibers 28 can range from between about 30% to about 85%, by weight, of the first absorbent 24. The second group of fibers 30 can range from between about 5% to about 20%, by weight, of the first absorbent 24. And the superabsorbent 32 can range from between about 10% to about 60%, by weight, of the first absorbent 24. It has been found that forming a first absorbent 24 with about 58% of the first group of fibers 28, about 10% of the second group of fibers 30, and about 32% of superabsorbent works well for absorbing and retaining urine.

The first group of fibers 28 should be present in the first absorbent 24 by a greater percent, by weight, than the second group of fibers 30. By using a greater percent of the first group of fibers 28 one can reduce the overall cost of the first absorbent 24. The first group of fibers 28 also ensures that the absorbent article 10 has sufficient fluid absorbing capacity. Cellulosic fibers 28, such as pulp fibers, are generally much cheaper than synthetic binder fibers 30. For good performance, the second group of fibers 30 should make up at least about five percent (5%) of the first absorbent 24, by weight to ensure that the first absorbent 24 has sufficient tensile strength. As stated above, the first absorbent 24 should be a mixture of the components 28, 30 and 32.

The first absorbent 24 is compressed in a substantially dry condition after heat curing at a temperature of about 165 degrees Celsius for a time of from between about 8 seconds to about 10 seconds to a density ranging from between about 0.09 grams per cubic centimeter g/cm$^3$ to about 0.3 g/cm$^3$. Preferably, the first absorbent 24 is compressed in a substantially dry condition to a density ranging from between about 0.15 g/cm$^3$ to about 0.22 g/cm$^3$. Most preferably, the first absorbent 24 is compressed in a substantially dry condition to a density of at about 0.2 (g/cm$^3$). This compression of the first absorbent 24 will assist in forming the thin absorbent article 10.

It is important to note that the stabilized material, making up the first and second absorbents, 24 and 26 respectively, should have sufficient tensile strength in the machine direction to allow winding it into rolls which can later be unwound and processed on converting equipment. Sufficient tensile strength can be achieved by varying the content of the binder fiber, adjusting the curing conditions, changing the specific density to which the fibers are compacted, as well as other ways known to one skilled in the art. It has been found that the first and second absorbents, 24 and 26 respectively, should have a tensile strength of at least 12 Newtons per 50 mm (N/50 mm). Preferably, the first and second absorbents, 24 and 26 respectively, should have a tensile strength of at least 18 N/50 mm. More preferably, the first and second absorbents, 24 and 26 respectively, should have a needed tensile strength of at least 25 N/50 mm. The tensile strength of the material can be tested using a tester, model MTS/Sintech 1/S which is commercially sold by MTS Systems Corporation having a mailing address of P.O. Box 14226, Research Triangle Park, N.C. The tensile strength at peak load for the purpose of this invention is measured by securing a 50 mm strip of stabilized material between two movable jaws of a tensile tester. A distance of about 10 cm initially separates the two jaws. The two jaws are then moved outward away from one another at a rate of 25 cm/minute until the strip of material breaks. The tensile strength is recorded as peak load.

Referring again to FIG. 2, the second absorbent 26 is arranged near the baffle 14 and is positioned vertically below the first absorbent 24. The second absorbent 26 can have a length that equals the length of the first absorbent 24 but preferably is sized to be slightly shorter than the length of the first absorbent 24. Most preferably, the second absorbent 26 will have a length that ranges from between about 60% to about 95% of the length of the first absorbent 24. The width of the second absorbent 26 should be less than the width of the first absorbent 24. Preferably, the width of the second absorbent 26 is from between about 40% to about 75% of the width of the first absorbent 24.

The second absorbent 26 is also a stabilized material, preferably an airlaid material, constructed of a blend of a first group of fibers 28, a binder 30, preferably in the form of a second group of fibers, and a superabsorbent 32. Preferably, the first and second absorbents, 24 and 26 respectively, are of similar composition. The compositions of the first and second absorbents, 24 and 26 respectively, can be identical, if desired. One difference between the first and second absorbents, 24 and 26 respectively, is that the second absorbent 26 has a basis weight which is equal to or greater than the basis weight of the first absorbent 24. By so constructing the second absorbent 26, one can be assured that the absorbent article 10 will have adequate absorbent capacity to function properly. Preferably, the basis weight of the second absorbent 26 is greater than the basis weight of the first absorbent 24. More preferably, the basis weight of the second absorbent 26 is at least 1.5 times greater than the basis weight of the first absorbent 24. Most preferably, the basis weight of the second absorbent 26 is at least 2 times greater than the basis weight of the first absorbent 24. The size, area, shape, etc. of the second absorbent 26 can be adjusted, such as by folding, slitting, cutting, using one or more layers, etc. to achieve the desired absorbent capacity.

It should be noted that when the first absorbent 24 is die cut into a shaped configuration, such as a dog bone shape, a certain amount of waste is created. Such waste will increase the cost to manufacture the absorbent article 10. Therefore, it is desirable to utilize a minimum basis weight for the first absorbent 24 in order to reduce waste. Since the second absorbent 26 has a generally rectangular configuration, it is more economical to increase the absorbent capacity of the absorbent article 10 by adjusting the area and/or the number of layers from which the second absorbent 26 is constructed.

Still referring to FIG. 2, one way of achieving the desired basis weight of the second absorbent 26 is depicted. In this figure, the second absorbent 26 is longitudinally folded upon itself into a U-shaped configuration. This folding of the second absorbent 26 doubles its basis weight.

Figure 4:
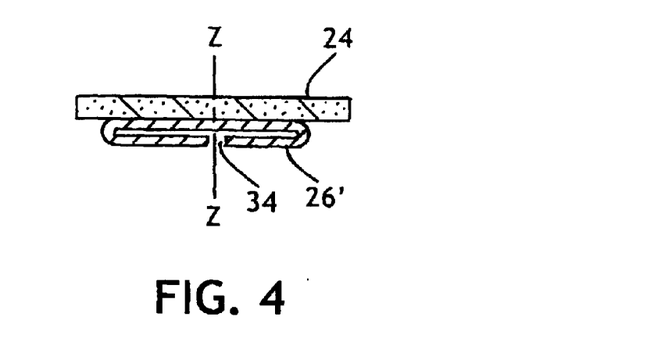
FIG. 4 is an alternative cross-sectional view of the first and second absorbents forming the absorbent core with the second absorbent being C-folded.
Figure 5:
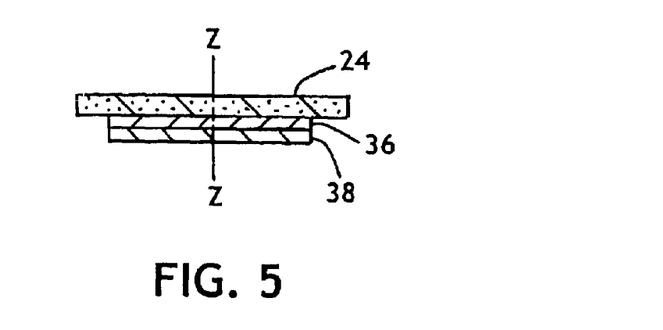
FIG. 5 is another alternative cross-sectional view of the first and second absorbents forming the absorbent core with the second absorbent being cut into two distinct layers.

Referring to FIGS. 4 and 5, two alternative ways to increase the basis weight of the second absorbent 26 while using the same material as was used for the first absorbent 24 are depicted. In FIG. 4, a second absorbent 26' is C-folded so as to have a channel or slit 34 formed which extends the length of the second absorbent 26' and which is aligned with the vertical axis z—z. The channel or slit 34 can face up or down. In FIG. 5, a third way of increasing the basis weight of a second absorbent is depicted while using a similar composition as was used for the first absorbent 24. In FIG. 5, the second absorbent is shown as two separate and distinct layers 36 and 38. The two layers 36 and 38 together will have a greater basis weight than the first absorbent 24 since all are formed from a similar composition or from the identical material.

It should be noted that if one desired to manufacture an absorbent article 10 having a lower fluid absorbent capacity, then one could construct the second absorbent 26 as a single layer.

Like the first absorbent 24, the second absorbent 26 has a predetermined basis weight ranging from between about 100 gsm to about 600 gsm. Preferably, the second absorbent 24 has a basis weight of from between about 300 gsm to about 600 gsm. Most preferably, the first absorbent 24 has a basis weight of about 400 gsm. Depending on the required absorbent capacity one wished for the finished absorbent article 10, the second absorbent 26 could be constructed to have a basis weight that is a whole number multiple, or an integral multiple, of the first absorbent 24.

As stated above, the first group of fibers 28 making up the second absorbent 26 can be cellulosic fibers, such as pulp fibers. The fibers within the first group of fibers 28 are short in length, have a high denier, and are hydrophilic. The first group of fibers 28 can be formed from 100% softwood fibers. Preferably, the first group of fibers 28 is southern pine Kraft pulp fibers having a length of about 2.5 mm. The fibers 28 should have a denier of greater than 2.0. The denier of cellulosic fibers can be determined as stated above. A suitable material to use for the first group of fibers 28 is Weyerhaeuser NB 416 pulp fibers.

Referring again to FIG. 1, the second absorbent 26 is depicted as being narrower in width than the first absorbent 24 and is shown having a generally rectangular configuration. The reason for the rectangular configuration is that some stabilized material, especially airlaid material, is relatively difficult to recycle. By forming the second absorbent 26 into a generally rectangular shape, one can minimize waste during the manufacturing process and produce a lower cost absorbent article 10. In addition, by constructing the first and second absorbents, 24 and 26 respectively, out of the same or similar composition, one can reduce one's inventory of raw materials and thereby reduce the cost required to manufacture the absorbent article 10.

The binder portion of the second absorbent 26 can be a chemical coating. Preferably, the binder portion of the second absorbent 26 will consist of a second group of fibers 30. The second group of fibers 30 are preferably synthetic binder fibers identical to those used to form the first absorbent 24. Preferably, the second group of fibers 30 are bicomponent fiber having a polyester core surrounded by a polyethylene sheath. Alternatively, the second group of fibers 30 are bicomponent fiber having a polypropylene core surrounded by a polyethylene sheath.

The fibers making up the second group of fibers 30 are longer in length and have a lower denier than the fibers making up the first group of fibers 28. The length of the fibers 30 can range from between about 3 mm to about 6 mm. A fiber length of 3 mm works well. The fibers 30 can have a denier equal to or less than 2.0. The fibers 30 should be moisture insensitive and can be either crimped or non-crimped. Crimped fibers are preferred since they are commercially available.

The second absorbent 26 also contains a superabsorbent 32. As explained above, a superabsorbent is a material capable of absorbing at least 10 grams of water per gram of superabsorbent material. The superabsorbent 32 is preferably in the shape of small particles, although fibers, flakes or other forms of superabsorbents can also be used. The superabsorbent 32 used in the second absorbent 26 can be identical in composition to the superabsorbent used in the first absorbent 24. A suitable superabsorbent 32 is FAVOR 880. FAVOR 880 is commercially available from Stockhausen, Inc. having an office located at 2408 Doyle Street Greensboro, N.C. 27406. Other similar types of superabsorbents, some of which are commercially available from Stockhausen Inc., can also be used. Preferably, the superabsorbent 32 is present from between about 10 weight percent to about 60 weight percent of the stabilized material.

The individual components 28, 30 and 32 of the second absorbent 26 can be present in varying amounts. However, it has been found that the following percentages work well in forming the thin absorbent article 10. The first group of fibers 28 can range from between about 30% to about 85%, by weight, of the first absorbent 24. The second group of fibers 30 can range from between about 5% to about 20%, by weight, of the first absorbent 24. And the superabsorbent 32 can range from between about 10 to about 60%, by weight, of the first absorbent 24. It has been found that forming a second absorbent 26 with about 58% of the first group of fibers 28, about 10% of the second group of fibers 30, and about 32% of superabsorbent works well for absorbing and retaining body fluid, especially urine.

The first group of fibers 28 should be present in the second absorbent 26 by a greater percent, by weight, than the second group of fibers 30 so as to reduce the overall cost of the second absorbent 26. Cellulosic fibers 28, such as pulp fibers, are generally much cheaper than synthetic binder fibers 30. For good performance, the second group of fibers 30 should make up at least about five percent (5%) of the second absorbent 26, by weight to ensure sufficient tensile strength. As stated above, the second absorbent 26 should be a mixture of the components 28, 30 and 32.

Like the first absorbent 24, the second absorbent 26 is compressed in a substantially dry condition after heat curing at a temperature of about 165 degrees Celsius for a time of from between about 8 seconds to about 10 seconds to a density ranging from between about 0.09 grams per cubic centimeter $g/cm^3$ to about 0.3 $g/cm^3$. Preferably, the second absorbent 26 is compressed in a substantially dry condition after heat curing as explained above to a density ranging from between about 0.15 $g/cm^3$ to about 0.22 $g/cm^3$. Most preferably, the second absorbent 26 is compressed in a substantially dry condition after heat curing as explained above to a density of about 0.2 ($g/cm^3$). This compression of the second absorbent 26 will assist in forming the thin absorbent article 10.

It should be noted that the first and second absorbents, 24 and 26 respectively, are preferably compressed to the same density during the manufacturing process.

Referring back to FIG. 2, the absorbent article 10 is shown having a thickness $t_1$ of less than about 5 mm. Preferably, the absorbent article 10 has a thickness $t_1$ of from between about 3 mm to about 5 mm. More preferably, the absorbent article 10 has a thickness $t_1$ of about 3.5 mm. The thickness $t_1$ or caliper of the absorbent article 10 can be determined by measuring the thickness $t_1$ of the absorbent article 10 with a bulk tester such as a Digimatic Indicator Gauge, type DF 1050E which is commercially available from Mitutoyo Corporation of Japan. Typical bulk testers utilize a smooth platen that is connected to the indicator gauge. The platen has dimensions that are smaller than the length and width of the second absorbent 26. The thickness of the absorbent article 10 is measured under a pressure of 0.35 kPa.

Still referring to FIG. 2, the absorbent core 16 also has a thickness $t_2$ of less than about 4 mm. Preferably, the absorbent core 16 has a thickness $t_2$ ranging from between about 2 mm to about 4 mm. More preferably, the absorbent core 16 has a thickness $t_2$ of less than about 3 mm. The thickness $t_2$ of the absorbent core 16 can be measured in a similar fashion as the thickness $t_1$ of the absorbent article 10 except that the absorbent core 16 will first be removed from the absorbent article 10.

The absorbent article 10 further is shown having a garment adhesive 40 secured to an exterior surface of the baffle 14. The garment adhesive 40 can be a hot or cold melt adhesive that functions to attach the absorbent article 10 to the inner crotch portion of an undergarment during use. The garment adhesive 40 enables the absorbent article 10 to be properly aligned and retained relative to the user's urethra so that maximum protection from the involuntary loss of urine can be obtained. The garment adhesive 40 can be slot coated onto the baffle 14 as one or more strips or it can be applied as a swirl pattern. The composition of the garment adhesive 40 is such that it will allow a user to remove the absorbent article 10 and reposition the article 10 in the undergarment if needed. A suitable garment adhesive 40 that can be used is Code Number 34-5602 which is commercially available from National Starch and Chemical Company. National Starch and Chemical Company has an office located at 10 Finderne Avenue, Bridgewater, N.J. 08807.

In order to protect the garment adhesive 40 from contamination prior to use, a releasable peel strip 42 is utilized. The peel strip 42 can be formed from paper or treated paper. A standard type of peel strip 42 is a white Kraft peel paper coated on one side so that it can be easily released from the garment adhesive 40. The user removes the peel strip 42 just prior to attaching the absorbent article 10 to the inner crotch portion of his or her undergarment. Three suppliers of the peel strips 42 include Tekkote, International Paper Release Products, and Namkyung Chemical Ind. Co., Ltd. Tekkote has an office located at 580 Willow Tree Road, Leonia, N.J. 07605. International Paper Release Products has an office located at 206 Garfield Avenue, Menasha, Wis. 54952. Namkyung Chemical Ind. Co., Ltd. has an office located at 202-68 Songsan-ri, Taean-eup, Hwaseoung-kum, Kyunggi, Korea.

The above description teaches the use of a stabilized material, such as airlaid, for the first and second absorbents, 24 and 26 respectively. However, the unique idea of using multiple plies of the same material will work for any material that possesses sufficient tensile strength to make it through the manufacturing and/or converting processes. The same econqmic principles of minimizing waste from the shaped first absorbent 24 while maintaining superabsorbent in that layer apply. Examples of other materials include using wet laid webs constructed of pulp fibers and superabsorbents. Examples of these materials are described in U.S. Pat. No. 5,651,862 issued to Anderson et al. Another material commercially sold by Rayonier Inc. of Jesup, Ga. is a high-density superabsorbent containing a non-stabilized web formed on tissue, which can be slit, folded and processed on a converting line. U.S. Pat. No. 5,916,670 issued to Tan et al. teaches this material. A third material is MegaThin® a high superabsorbent containing composite produced by JATI (Japan Absorbent Technology Institute). MEGATHIN is a registered trademark of JATI.

EXAMPLES

The following examples are presented to more fully describe this invention and should not be interpreted as limiting the invention in any way.

Stabilized airlaid composites were manufactured by Concert Industries, of Thurso, Quebec. The composites included 10% KoSa T255 binder fiber (6 mm, 2 denier), 30% FAVOR 880 superabsorbent and 60% Weyerhaeuser NB-416 pulp. The material was passed through an oven at 165 degrees Celsius for about 10 seconds to cure the binder fiber. The material was immediately passed under a compacting roll, constructed from steel, to achieve a density of about 0.175 g/cc. Basis weights of 300 gsm, 200 gsm and 175 gsm were manufactured. Absorbent cores 16 were assembled in a fashion similar to that depicted in FIG. 4 and the absorbent capacities were assessed. The absorbent capacity was measured by weighing the dry absorbent cores 16. The absorbent cores 16 were then soaked in 0.9%, by weight, sodium chloride in deionized water for 20 minutes and then placed on a vacuum box under a latex sheet for 5 minutes. During this time, the vacuum box was set to subject the absorbent cores 26 to a pressure of 3.45 kPa in order to squeeze excess liquid from the absorbent cores 16. The wet absorbent cores 16 were then weighed and the dry weight was subtracted to obtain the retention capacity.

Example 1

The first absorbent 24 was a single layer formed into a dog bone configuration and had a basis weight of 300 gsm, a tensile strength of 68 N/50 mm and an area of 81.5 cm$^2$. The second absorbent 26 was a single layer formed into a rectangular configuration and had a basis weight of 300 gsm and an area of 50.8 cm$^2$. The absorbent capacity of this combined absorbent core was 47 grams.

Example 2

The first absorbent 24 was a single layer formed into a dog bone configuration and had a basis weight of 200 gsm, a tensile strength of 43 N/50 mm and an area of 81.5 cm$^2$. The second absorbent 26 included two layers formed into a rectangular configuration and had a basis weight of 400 gsm (200 gsm per layer) and an area of 50.8 cm$^2$. The absorbent capacity of this combined absorbent core was 47 grams. Since the first absorbent 24 contained a basis weight of 200 gsm instead of 300 gsm, the waste during manufacturing was reduced by 33% while maintaining the same absorbent capacity for the absorbent core 16.

Example 3

The first absorbent 24 was a single layer formed into a dog bone configuration and had a basis weight of 175 gsm, a tensile strength of 33 N/50 mm and an area of 81.5 cm$^2$. The second absorbent 26 included two layers formed into a rectangular configuration and had a basis weight of 350 gsm (175 gsm per layer) and an area of 50.8 cm$^2$. The absorbent capacity of this combined absorbent core was 43 grams. By manipulating basis weight, the absorbent capacity can be controlled. Compare example 2 to example 3.

All of the examples used materials of identical compositions for the first and second absorbents, 24 and 26 respectively. The absorbent article 10 can be manufactured according to the method described below.

Method

A method of manufacturing the absorbent article 10 will now be described. The method includes the steps of forming the first absorbent 24 from a stabilized material, such as an airlaid. The airlaid will contain a superabsorbent and have a predetermined basis weight. The airlaid material can be a rectangular, elongated strip having a transverse width of about 30 mm to 100 mm. The airlaid can be unwound from a supply roll and be fed into a cutter that can cut the elongated strip into individual members. The periphery of the first absorbent 24 can be cut, for example by a die cutter, into a shaped configuration, such as a dog bone shape, an hourglass shape, an oval shape, etc.

The method further includes the step of forming the second absorbent 26 from a similar or identical stabilized material. Preferably, the stabilized material will also be an airlaid containing superabsorbent and having a predetermined basis weight. Preferably, the first and second absorbents, 24 and 26 respectively, will be formed from the same airlaid material. The airlaid can be a rectangular, elongated strip having a transverse width of between about 30 mm to about 100 mm. Preferably, the second absorbent will be formed from a strip of stabilized material having the same width as was used to form the first absorbent 24. The airlaid can be unwound from a supply roll and doubled in thickness in at least three different ways in order to increase the basis weight of the second absorbent 26. One way is to C-fold each individual segment into a generally rectangular shape. The C-fold can have a channel or slit 34 that appears either at the top or bottom of the C-fold. A second way is to fold each individual segment upon itself into a U-shape. The opening of the U-shape can face either to the left or to the right. A third way is to slice or slit each individual segment longitudinally into two strips. The two strips are then placed one on top of the other. Regardless of the method used to form the second absorbent 26, the second absorbent 26 should have a width that is less than the narrowest width of the first absorbent 24. The second absorbent 26, after being doubled in thickness, can be routed to a cutter. The cutter can consist of a knife roll and a cooperating anvil roll. Here, the airlaid material is cut into individual rectangular segments.

The second absorbent 26 will have a basis weight which is at least equal to, and preferably, greater than the basis weight of the first absorbent 24. The reason for this is that by controlling the basis weight of the second absorbent 26, one can be assured that the second absorbent 26 will be able to retain at least an equal if not greater quantity of body fluid than the first absorbent 24. By retaining a majority of the body fluid in the second or lower absorbent 26, which is located away from the body of the wearer, the first absorbent 24 will be drier. This feature creates a more comfortable absorbent article 10 that will feel drier to the user and also minimizes design waste.

Regardless of which of the three options for forming the second absorbent 26 are utilized, the method then includes the step of arranging the second absorbent 26 directly beneath and in direct contact with the first absorbent 24. When the second absorbent 26 is slit into two individual layers, both layers are positioned below the first absorbent 24. It is preferred that the second absorbent 26 be narrower in width than the first absorbent 24. More preferably the second absorbent 26 will have a smaller surface area than the first absorbent 24. Construction adhesive can be used between the first and second absorbents, 24 and 26 respectively, if needed.

It should be noted that the airlaid material could be initially, longitudinally slit into equal widths, for example 65 mm. The first and second absorbents, 24 and 26 respectively, would then be formed from these similar width elongated strips. This would simplify production since only one specific airlaid material has to be made. Ideally, forming the absorbent core 16 out of a single airlaid material would simplify the supply chain and further reducing manufacturing cost.

The absorbent core 16, formed from the first and second absorbents, 24 and 26 respectively, is then combined with a liquid permeable liner 12 and a liquid-impermeable baffle 14 to form an absorbent article 10. A transfer layer 22 can be included in the assembling process, if desired.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A method of forming an absorbent core comprising the steps of:
   a) forming a first absorbent into a shaped configuration from an elongated strip of a stabilized airlaid material constructed of a blend of a first group of fibers, a binder and a superabsorbent, said first adsorbent having a predetermined basis weight and being compressed in a substantially dry condition after being heat cured at a temperature of about 165 degrees Celsius for a time of from between about 8 seconds to about 10 seconds to a density ranging from between about 0.09 g/cm$^3$to about 0.3 g/cm$^3$.
   b) forming a second absorbent of double its thickness from an elongated strip of stabilized material, said stabilized material containing a superabsorbent, said second absorbent having a basis weight which is greater than the basis weight of said first absorbent;
   c) positioning said second absorbent directly below and in contact with said first absorbent to form said absorbent core; and
   d) wherein said stabilized material used to form said first and second absorbents is the same composition.

2. The method of claim 1 wherein said first absorbent is formed with a die cutter.

3. The method of claim 1 wherein said secondabsorbent is doubled in thickness by C-folding said second absorbent.

4. The method of claim 1 wherein said second absorbent is doubled in thickness by U-folding said second absorbent.

5. The method of claim 1 wherein said second absorbent is doubled in thickness by slitting said second absorbent into two strips and placing the two strips one on top of the other.

6. A method of forming an absorbent core comprising the steps of:
   a) forming a first absorbent into a shaped configuration from an elongated strip of a stabialized airlaid material constructed of a blend of a first group of fibers, a binder and a superabsorbent, said first absorbent having a predetermined basis weight;
   b) forming a second absorbent from an elongated strip of a stabilized airlaid material constructed of a blend of a first group of fibers, a binder and a superabsorbent, said second absorbent having an initial thickness and slitting said second absorbent into two layers and positioning one layer above the other layer to form a thickness that is doubled that of said initial thickness, and said second absorbent having a basis weight which is greater than the basis weight of said first absorbent; and
   c) positioning said second absorbent directly below and contact with said first absorbent to fomr said absorbent core.

7. The method of claim 6 wherein said stabilized airlaid material used to form said first and second absorbents is the same composition and said first absorbent is compressed in a substantially dry condition after being heat cured at a temperature to about 165 degrees Celsius for a time of from between about 8 to about 10 seconds to a density ranging from between about 0.09 g/cm $^3$to about 0.3.g/cm$^3$.

8. The method of claim 6 wherein said said basis weight of said second absorbent is at least 1.5 times greater than said basis weight of said first absorbent.

9. The method of claim 6 wherein said first absorbent is formed with a die cutter.

10. The method of claim 6 wherein said second absorbent is doubled in thickneess by C-folding said second absorbent.

11. The method of claim 6 wherein said second absorbent is doubled in thickness by C-folding said second absorbent.

12. The method of claim 6 wherein said second absorbent is doubled in thickness by sitting said second absorbent into two strips and placing the two strips one on top of the other.

13. A method of forming an absorbent core comprising the steps of:
   a) forming a first absorbent into a shaped configuration from an elongated strip of a stabilized airlaid material constructed of a blend of a first group of fibers, a binder and a superabsorbent, said first absorbent having a predetermined basis weight;
   b) forming a second absorbent from an elongated stabilized airlaid material which is constructed of a blend of a first group of fibers, a binder and a superabsorbent, said second absorbent having an initial thickness and arranging said second absorbent upon itself to double said initial thickness, and said second absorbent having a basis weight which is at least 1.5 times greater than the basis weight of said first absorbent; and c) positioning said second absorbent directly below and in contact with said first absorbent to form said absorbent core.

14. A method of forming an absorbent core comprising the steps of:

a) forming a first absorbent into a shaped configuration from an elongated strip of a stabilized airlaid material constructed of a blend of a first group of fibers, a binder and a superabsorbent, said first absorbent having a predetermined basis weight; 'b) forming a second absorbent from an elongated strip of a stabilized airlaid material constructed of a blend of a first group of fibers, a binder and a superabsorbent, said second absorbent having an initial thickness and arranging said second absorbent upon itself to double said initial thickness, and said second absorbent having a basis weight which is at least 2 times greater than the basis weight of said first absorbent; and c) positioning said second absorbent directly below and in contact with said first absorbent to form said absorbent core.

* * * * *